United States Patent [19]

Nishikawa et al.

[11] 4,299,800

[45] Nov. 10, 1981

[54] METHOD OF REMOVING OXYGEN FROM A GAS CONTAINING AN UNSATURATED HYDROCARBON

[75] Inventors: Eiichiro Nishikawa; Masuo Shinya; Hiroshi Furukawa; Katsumi Kaneko, all of Saitama, Japan

[73] Assignee: Toa Nenryo Kogyo Kabushiki Kaisha, Tokyo, Japan

[21] Appl. No.: 209,168

[22] Filed: Nov. 21, 1980

[30] Foreign Application Priority Data

Dec. 28, 1979 [JP] Japan .............................. 54-170327

[51] Int. Cl.³ ............................................. B01D 53/36
[52] U.S. Cl. .................................... 423/219; 423/248; 585/841
[58] Field of Search ............... 423/210, 219, 245, 248; 585/841

[56] References Cited

U.S. PATENT DOCUMENTS

| | | | |
|---|---|---|---|
| 1,960,212 | 5/1934 | Walker | 423/219 |
| 3,033,642 | 5/1962 | Buksta et al. | 423/219 |
| 3,055,732 | 9/1962 | Delassus et al. | 423/219 |
| 3,305,597 | 2/1967 | Straschil et al. | 585/841 |
| 3,420,618 | 1/1969 | Fleming | 423/219 |
| 3,480,384 | 11/1969 | Hardison | 423/219 |

FOREIGN PATENT DOCUMENTS 49-25241 6/1974 Japan .................................. 585/841

OTHER PUBLICATIONS

Derwent Abstract of Japanese Patent Application OPI No. 148684/1976 & 149207/1976.

*Primary Examiner*—Earl C. Thomas
*Attorney, Agent, or Firm*—Rebecca Yablonsky

[57] ABSTRACT

This invention consists essentially in a method of removing oxygen from a gas containing an unsaturated hydrocarbon, which comprises contacting a gas containing an unsaturated hydrocarbon and oxygen with silver and/or gold, or a catalyst containing at least one of them, in the presence of hydrogen.

9 Claims, No Drawings

METHOD OF REMOVING OXYGEN FROM A GAS CONTAINING AN UNSATURATED HYDROCARBON

BACKGROUND OF THE INVENTION

This invention relates to a method of removing oxygen from a gas containing an unsaturated hydrocarbon, and more particularly, to a method for removing oxygen selectively by hydrogenation from a gas containing an unsaturated hydrocarbon, particularly an olefin such as ethylene and propylene.

The oxygen existing as impure matter in a gas containing an unsaturated hydrocarbon must be removed, since it is likely to bring about a number of problems during the handling of the gas, or the recovery of the hydrocarbon therefrom. Accordingly, a number of methods have heretofore been proposed for removing oxygen from a gas containing an unsaturated hydrocarbon.

The prior methods of removing oxygen from olefins include, for example, a method which removes oxygen selectively by adsorption by contacting the gas with an alkali metal amide in ammonia (Japanese Patent Publication No. 3860/1962), or with a resin containing copper as obtained by reducing a high molecular complex compound composed of a high molecular compound and a copper salt (Japanese Patent Application Laid-Open Specification No. 148684/1976); and a method which removes oxygen by hydrogenation, while controlling the hydrogenation of the olefin, by contacting the gas with a molybdenum sulfide catalyst on α-alumina in the presence of hydrogen (Japanese Patent Publication No. 25241/1974), with a copper catalyst in the presence of hydrogen (Japanese Patent Publication No. 25241/1974), with an activated nickel catalyst in the presence of hydrogen (Japanese Patent Application Laid-Open Specification No. 149207/1976), or with a catalyst composed of a metal of the platinum group, while a sulfur compound is being added thereinto, in the presence of hydrogen (U.S. Pat. No. 3,480,384).

The known methods based on adsorption require the regeneration of the adsorbent, while those which are based on hydrogenation involve difficulty in the selective hydrogenation of oxygen alone, and disadvantageously bring about considerable loss of the olefin by hydrogenation.

Applicants have developed a method for removing oxygen selectively by hydrogenation from a gas containing an olefin and oxygen, without involving any hydrogenation of the olefin.

SUMMARY OF THE INVENTION

This invention consists essentially in a method of removing oxygen from a gas containing an unsaturated hydrocarbon, which comprises contacting a gas containing an unsaturated hydrocarbon and oxygen with silver and/or gold, or a catalyst containing at least one of them, in the presence of hydrogen.

DETAILED DESCRIPTION

According to this invention, silver and gold perform a catalytic action, and may be used either individually or together. Silver is more suitable than gold. The metals may be used as they are, or in the form of their compounds. It is preferable to use a catalyst composed of any such metal or a compound thereof supported appropriately on a carrier. Examples of suitable silver compounds include silver nitrate, silver sulfate, silver carbonate, silver nitrite, silver phosphate, silver chloride, silver iodide, silver bromide, silver chlorate, silver perchlorate, silver thiosulfate, silver sulfide, silver oxide, silver cyanide, silver hydroxide, silver oxalate and silver acetate. Silver nitrate is most suitable. Examples of suitable gold compounds include aurous chloride, auric chloride, chloroauric acid, gold cyanide, gold hydroxide, and a chloroaurate such as sodium, potassium or ammonium chloroaurate. It is preferred to use chloroauric acid or a chloroaurate.

It is possible to use alumina, silica-alumina, silica, zeolite, diatomaceous earth, zirconia, titania, magnesia active carbon, or the like as a carrier for the catalyst for use in this invention. Alumina, silica-alumina and silica are preferred.

The carrier supports usually 0.01 to 50% by weight, and preferably 0.1 to 20% by weight, of either metal, whether the metal is applied in its elemental form, or in the form of a compound thereof, though the amount of the metal depends on the kinds of the metal and the carrier selected.

For the purpose of this invention, unsaturated hydrocarbons means olefins, diolefins and acetylenes, and more specifically, ethylene, propylene, isobutene, n-butene, butadiene, acetylene, and other hydrocarbons which are in gaseous form at room temperature and atmospheric pressure, but also includes olefins, diolefins or the like containing 5 to 12 carbon atoms.

The method of this invention is applicable to gases containing an olefinic hydrocarbon and oxygen. The gases may also contain a saturated hydrocarbon, a diolefin, nitrogen, carbon dioxide, carbon monoxide, argon, helium or the like. They may also contain a small amount of a sulfur compound. Examples of these gases include ethylene or propylene containing a small amount of oxygen, a by-product gas resulting from petroleum refining, a gas from pyrolysis of petroleum, catalytic cracking, steam cracking, or reforming, and containing ethylene or propylene, and a coke oven gas.

The method of this invention is preferably applied to a gas having an oxygen concentration which does not amount to the explosion limit of the gas. If the method is used for a gas having an oxygen concentration which amounts to its explosion limit, it is desirable to incorporate steam, nitrogen or other inert gas into the gas to reduce its oxygen concentration until it does not amount to the explosion limit of the gas.

This invention can be put into practice by contacting a gas containing an unsaturated hydrocarbon and oxygen with the aforementioned catalyst in the presence of hydrogen. The ratio of the gas to hydrogen depends on the quantity of oxygen in the gas, and it is sufficient to use such a quantity of hydrogen as is theoretically required for complete hydrogenation of the oxygen in the gas to be treated. It is, however, desirable to employ an excess quantity of hydrogen, as it does not promote the hydrogenation of the olefin present in the gas.

The reaction involved in the method of this invention is caused to take place at a temperature of 0° C. to 400° C., preferably in the range from room temperature to 300° C., and more preferably from 50° C. to 200° C. It is usually more than sufficient to cause the reaction to take place at atmospheric pressure, though the reaction under pressure up to, say, 30 kg/cm² does not cause any problem. The reaction is usually caused to take place in a continuous vapor phase system, but may also be accomplished in a batch system.

The mixture of the gas to be treated and hydrogen, and the catalyst have a ratio which is selected to provide a gaseous hourly space velocity (GHSV) of usually 100 to 100,000, and preferably 500 to 10,000, if the reaction is caused to take place in a continuous vapor phase system.

The use of the method of this invention as hereinabove described most advantageously makes it possible to remove oxygen alone, by hydrogenation, from a gas containing an unsaturated hydrocarbon and oxygen without any appreciable loss of the hydrocarbon by hydrogenation.

The invention will now be described in further detail with reference to the following examples, which do not limit the scope of this invention.

EXAMPLE 1

A commercially available type of alumina having a specific surface area of 189 $m^2/g$ was immersed in an aqueous solution of silver nitrate, and left there for three hours. Then the greater part of the solution was evaporated by heating, and after the residue was dried at 110° C. for 16 hours, it was calcined in air at 500° C. for 12 hours, whereby a catalyst carrying 5% by weight of silver was prepared.

Then, 6 cc of the catalyst thus obtained were placed in a reaction tube, and a gaseous mixture consisting of 16.5% by volume of ethylene, 9.2% by volume of hydrogen, 1.5% by volume of carbon monoxide, 0.3% by volume of oxygen and 72.5% by volume of nitrogen was fed into the reaction tube at the temperatures shown in Table 1 and a GHSV of 1,000 V/H/V, whereby the reaction was conducted. The gas leaving the outlet of the reaction tube was analyzed, and the results shown in Table 1 were obtained.

COMPARATIVE EXAMPLE 1

A catalyst carrying 5% by weight of copper was prepared by repeating the procedures set forth in Example 1, except that copper nitrate was used instead of silver nitrate. A reaction was conducted at the temperatures shown in Table 1 in the presence of the catalyst thus obtained by repeating the procedures of Example 1. The results shown in Table 1 were obtained.

EXAMPLE 2

The same type of alumina as used in Example 1 was immersed in an aqueous solution of chloroauric acid for 12 hours, and after it was washed with water and dried at 110° C. for 16 hours, it was calcined in air at 500° C. for 12 hours, whereby a catalyst carrying 0.5% by weight of gold was prepared. This catalyst was used for the reaction at the temperatures shown in Table 1 by repeating the procedures set forth in Example 1. The results thereby obtained are shown in Table 1.

COMPARATIVE EXAMPLES 2 to 5

The reaction was conducted at the temperatures shown in Table 1 by repeating the procedures set forth in Example 1, except that the following four types of commercially available catalysts were used instead of the silver catalyst employed in Example 1, and the results shown in Table 1 were obtained:

A (Comparative Example 2): Toyo CCI's palladium catalyst for removing oxygen (carrying 0.1% by weight of palladium on alumina);

B (Comparative Example 3): Engelhard's platinum catalyst (carrying 0.5% by weight of platinum on alumina);

C (Comparative Example 4): Engelhard's rhodium catalyst (carrying 0.5% by weight of rhodium on alumina); and D (Comparative Example 5): Engelhard's ruthenium catalyst (carrying 0.5% by weight of ruthenium on alumina).

COMPARATIVE EXAMPLE 6

A catalyst carrying 5% by weight of vanadium was prepared by repeating the procedures set forth in Example 1, except that alumina was immersed in a solution of ammonium metavanadate in oxalic acid which contained 2 mols of oxalic acid per mol of ammonium metavanadate. A reaction was caused to take place at the temperatures shown in Table 1 by using the vanadium catalyst thus obtained, and otherwise repeating the procedures set forth in Example 1. The results thereby obtained are shown in Table 1.

COMPARATIVE EXAMPLE 7

A catalyst carrying 5% by weight of manganese was prepared by repeating the procedures set forth in Example 1, except that manganese acetate was used instead of silver nitrate.

A reaction was conducted at the temperatures shown in Table 1 by using the catalyst thus obtained, and otherwise repeating the procedures set forth in Example 1. The results thereby obtained are shown in Table 1.

COMPARATIVE EXAMPLE 8

A catalyst carrying 5% by weight of bismuth was prepared by repeating the procedures set forth in Example 1, except that alumina was immersed in a solution obtained by dissolving bismuth nitrate in 12% nitric acid. A reaction was conducted at the temperatures shown in Table 1 by using the catalyst thus obtained, and otherwise repeating the procedures set forth in Example 1. The results obtained therefrom are shown in Table 1.

COMPARATIVE EXAMPLE 9

A catalyst carrying 5% by weight of cobalt was prepared by repeating the procedures set forth in Example 1, except that cobalt nitrate was used instead of silver nitrate. A reaction was conducted at the temperatures shown in Table 1 by using the catalyst thus obtained, and otherwise repeating the procedures set forth in Example 1. The results obtained therefrom are shown in Table 1.

COMPARATIVE EXAMPLE 10

A catalyst carrying 0.5% by weight of iridium was prepared by repeating the procedures set forth in Example 1, except that iridic acid chloride was used instead of silver nitrate. A reaction was conducted at the temperatures shown in Table 1 by using the catalyst thus obtained, and otherwise repeating the procedures set forth in Example 1. The results obtained therefrom are shown in Table 1.

It will be obvious from Table 1 that according to the method employing the catalyst of this invention, the reaction is conducted selectively for oxygen along, with only a very small amount of conversion of ethylene, as opposed to the cases in which any other catalyst is used.

EXAMPLE 3

A gaseous mixture consisting of 9.4% by volume of hydrogen, 2.3% by volume of carbon monoxide, 0.1% by volume of carbon dioxide, 11.7% by volume of nitrogen, 200 ppm by volume of oxygen, 32.1% by volume of methane, 12.4% by volume of ethylene, 18.0% by volume of ethane, 9.2% by volume of propylene, 3.4% by volume of propane, 0.7% by volume of butene and 0.7% by volume of butane was reacted under the conditions shown in Table 2 and at atmospheric pressure in the presence of the silver catalyst used in Example 1, and otherwise by repeating the procedures set forth in Example 1. The results shown in Table 2 were obtained.

As is obvious from Table 2, the complete or nearly complete oxygen conversion was obtained, while the olefins such as ethylene and propylene showed only a trace of conversion.

EXAMPLE 5

A catalyst carrying 1% by weight of silver was prepared by repeating the procedures set forth in Example 1, and tested for the reaction at 100° C. in accordance with the procedures of Example 1. As the result, the conversion of the oxygen amounted to 99.4%, while the ethylene showed only a trace of conversion.

EXAMPLE 6

A catalyst carrying 20% by weight of silver was prepared by repeating the procedure set forth in Example 1, and tested for the reaction at 200° C. in accordance with the procedures of Example 1. As the result, the conversion of the oxygen amounted to 97.6%, while the ethylene showed only a trace of conversion.

What is claimed is:

1. A method of removing oxygen from a gas containing an unsaturated hydrocarbon, which comprises contacting a gas contacting an unsaturated hydrocarbon and oxygen with silver and/or gold, or a catalyst containing at least one of them, in the presence of hydrogen.

2. The method of claim 1 in which the silver and/or gold is supported on a carrier.

3. The method of claim 2 in which the carrier is selected from the group consisting of alumina, silica-alumina, silica, zeolites, diatomaceous earth, zirconia, titania, magnesia and activated carbon.

4. The method of claim 3 in which the carrier is alumina, silica-alumina or silica.

5. The method of claim 1 in which the unsaturated hydrocarbon comprises ethylene and/or propylene.

6. The method of claim 1 in which the contacting is carried out at a temperature in the range of 50° C. to 200° C.

7. The method of claim 6 in which the gaseous hourly space velocity is 100 to 100,000.

8. The method of claim 7 in which the gaseous hourly space velocity is 500 to 10,000.

9. The method of claim 1, 5 or 6 in which the contacting is carried out with alumina carrying silver.

TABLE 1

| | Conv. (%) Temp. (°C.) Catalyst | Oxygen | | | | | Ethylene | | | | |
|---|---|---|---|---|---|---|---|---|---|---|---|
| | | 50 | 100 | 150 | 200 | 300 | 50 | 100 | 150 | 200 | 300 |
| Example 1 | 5% Ag/Al$_2$O$_3$ | 99.5 | 99.5 | | 99.5 | | Trace | Trace | | 4.5 | |
| 2 | 0.5% Au/Al$_2$O$_3$ | | 29.7 | | 97.8 | | | Trace | | 1.9 | |
| Comp. Ex. 1 | 5% Cu/Al$_2$O$_3$ | 98.6 | 98.5 | 99.6 | 99.4 | | 0.9 | 53.2 | 83.9 | 86.7 | |
| 2 | 0.1% Pd/Al$_2$O$_3$ | | 99.3 | | | | | 15.1 | | | |
| 3 | 0.5% Pt/Al$_2$O$_3$ | 29.8 | 52.9 | | 98.7 | | Trace | 0.2 | | 45.7 | |
| 4 | 0.5% Rh/Al$_2$O$_3$ | 11.0 | 53.9 | | 99.0 | | Trace | Trace | | 14.3 | |
| 5 | 0.5% Ru/Al$_2$O$_3$ | 3.8 | 77.3 | | 99.4 | | Trace | 0.2 | | 11.2 | |
| 6 | 5% V/Al$_2$O$_3$ | | 2.7 | 10.2 | 89.9 | 99.1 | | Trace | 4.7 | 3.2 | 2.7 |
| 7 | 5% Mn/Al$_2$O$_3$ | | 4.9 | 10.3 | 61.8 | 99.3 | | Trace | 0.5 | 6.1 | 9.4 |
| 8 | 5% Bi/Al$_2$O$_3$ | | 3.0 | | 39.8 | 99.3 | | Trace | | 1.6 | 9.5 |
| 9 | 5% Co/Al$_2$O$_3$ | | 2.8 | | 63.4 | 98.2 | | Trace | | 2.6 | 10.0 |
| 10 | 0.5% Ir/Al$_2$O$_3$ | | Trace | | 74.6 | 98.8 | | Trace | | 2.6 | 11.0 |

TABLE 2

| Reaction Temp. (°C.) | GHSV (V/H/V) | Conversion of Oxygen (%) | Conversion of Olefins (%) | | |
|---|---|---|---|---|---|
| | | | Ethylene | Propylene | Butene |
| 50 | 3,600 | 88.2 | Trace | Trace | Trace |
| 50 | 1,000 | 95.3 | " | " | " |
| 100 | 3,600 | 100 | " | " | " |

EXAMPLE 4

A gaseous mixture consisting of 90.0% by volume of ethylene, 1,100 ppm of volume of oxygen, 2.5% by volume of hydrogen and 7.4% by volume of nitrogen was reacted in the presence of the silver catalyst used in Example 1 at atmospheric pressure, 100° C. and a GHSV of 1,000 V/H/V, and also as described in Example 1. As the result, the conversion of the oxygen amounted to 99.3%, while the ethylene showed a conversion of only 1.2%.

UNITED STATES PATENT OFFICE
CERTIFICATE OF CORRECTION

Patent No. 4,299,800  Dated November 10, 1981

Inventor(s) Eiichiro Nishikawa et al.

It is certified that error appears in the above-identified patent and that said Letters Patent are hereby corrected as shown below:

In claim 1, at column 6, line 37, after "gas" change "contacting" to -- containing --.

Signed and Sealed this

First Day of February 1983

[SEAL]

Attest:

Attesting Officer

GERALD J. MOSSINGHOFF

Commissioner of Patents and Trademarks